(12) United States Patent
Zeng et al.

(10) Patent No.: US 11,963,989 B2
(45) Date of Patent: *Apr. 23, 2024

(54) APPLICATION OF MEDICAL CELL CMU-PB-7 IN PREPARATION OF BLOOD LIPID-LOWERING DRUGS

(71) Applicants: Guangdong Xinghai Biotechnology Co., Ltd., Dongguan (CN); Guangdong Xinghai Institute of Cell, Dongguan (CN)

(72) Inventors: Jincheng Zeng, Dongguan (CN); Shaobing Zhang, Dongguan (CN)

(73) Assignees: GUANGDONG XINGHAI BIOTECHNOLOGY CO., LTD., Dongguan (CN); GUANGDONG XINGHAI INSTITUTE OF CELL, Dongguan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/336,973

(22) Filed: Jun. 17, 2023

(65) Prior Publication Data
US 2023/0330166 A1  Oct. 19, 2023

(30) Foreign Application Priority Data
Aug. 5, 2022 (CN) .......................... 202210939570.1

(51) Int. Cl.
| | | |
|---|---|---|
| *A61K 35/747* | (2015.01) | |
| *A61P 1/16* | (2006.01) | |
| *A61P 3/06* | (2006.01) | |
| *A61P 3/10* | (2006.01) | |
| *C12N 1/20* | (2006.01) | |
| *C12R 1/225* | (2006.01) | |

(52) U.S. Cl.
CPC .............. *A61K 35/747* (2013.01); *A61P 1/16* (2018.01); *A61P 3/06* (2018.01); *A61P 3/10* (2018.01); *C12N 1/205* (2021.05); *C12R 2001/225* (2021.05)

(58) Field of Classification Search
None
See application file for complete search history.

(56) References Cited

U.S. PATENT DOCUMENTS

2018/0117102 A1* 5/2018 Chung ................. A61K 35/744

FOREIGN PATENT DOCUMENTS

CN          114717147 A       7/2022

OTHER PUBLICATIONS

Park et al., Cholesterol-lowering effect of Lactobacillus rhamnosus BFE5264 and its influence on the gut microbiome and propionate level in a murine model, PLoS One, vol. 13(8), pp. 1-15. (Year: 2018).*
Che Zhengping et al., Research progress of hypolipidemic probiotics and its mechanism, Prog in Microbiol Immunol, Aug. 2022, vol. 50 No. 4, p. 88-95, Considered EN abstract.
CNIPA, Notification of First Office Action for Chinese application CN202210939570.1, dated Jan. 20, 2023.
CNIPA, Notification to grant patent right for Chinese application CN202210939570.1, dated Mar. 12, 2023.

* cited by examiner

*Primary Examiner* — Michelle F. Paguio Frising
*Assistant Examiner* — Grant C Currens
(74) *Attorney, Agent, or Firm* — Zhigang Ma

(57) ABSTRACT

The present invention discloses an application of a medical cell CMU-pb-7 in preparation of blood lipid-lowering drugs, which belongs to the technical field of biology. The medical cell CMU-pb-7 disclosed by the present invention is a newly discovered strain of *Lactobacillus rhamnosus*, having a collection number of CCTCC NO: M 2022220. The medical cell CMU-pb-7 of the present invention can relieve impaired glucose tolerance caused by a high-fat diet in mice with hyperlipidemia, reduce the blood lipid level, enhance the antioxidant capacity of the liver tissue, and regulate the expression of key proteins of liver lipid metabolism to relieve fatty change caused by a high-fat diet. The medical cell CMU-pb-7 disclosed by the present invention has a great potential application prospect in preparation of blood lipid-lowering drugs.

1 Claim, 26 Drawing Sheets

APPLICATION OF MEDICAL CELL CMU-PB-7 IN PREPARATION OF BLOOD LIPID-LOWERING DRUGS

CROSS REFERENCE TO RELATED APPLICATION

This patent application claims the benefit and priority of Chinese Patent Application No. 2022109395701 filed on Aug. 5, 2022, the disclosure of which is incorporated by reference herein in its entirety as part of the present application.

TECHNICAL FIELD

The present invention relates to the technical field of biology, and more particularly to an application of a medical cell CMU-pb-7 in preparation of blood lipid-lowering drugs.

BACKGROUND

Hyperlipidemia is a disease in which the blood lipid level changes abnormally due to the disorder of lipid metabolism, mainly manifested as increase in the concentrations of total cholesterol (TC), triglycerides (TG) and low-density lipoprotein cholesterol (LDL-C) and decrease in the concentration of high-density lipoprotein cholesterol (HDL-C). According to the latest epidemiological survey, the number of people with dyslipidemia in China has exceeded 400 million, and the prevalence rate is as high as 40.4%, among which people over 35 years old have the overall prevalence rate of dyslipidemia of 34.7% and the treatment rate of 7.8%. The disease tends towards younger people and seriously endangers national health. Hyperlipidemia and relevant cardiovascular diseases can be effectively controlled by regulating the disorder of lipid metabolism.

Medical cells mainly include functional probiotics, immunocytes, mesenchymal stem cells, etc. Probiotics is a hot topic in current medical cell research. Probiotics are a kind of active microorganisms beneficial to human health. When ingested in sufficient quantities, probiotics can colonize in the intestinal tract of the host, regulate intestinal microecological balance and blood lipid metabolism, and play a probiotic role. At present, medical cell type probiotics mainly include *Lactobacillus, Bifidobacterium, Sacchromyces*, etc. *Lactobacillus* probiotics have been used more and more widely in clinical applications, and *Lactobacillus rhamnosus* is one of the common *Lactobacillus*, which has the functions of regulating intestinal flora and improving body immunity.

Therefore, the problem to be urgently solved by those skilled in the art is to provide an application of a medical cell CMU-pb-7 in preparation of blood lipid-lowering drugs.

SUMMARY

In view of this, the present invention provides an application of a medical cell CMU-pb-7 in preparation of blood lipid-lowering drugs.

To achieve the above purpose, the present invention adopts the following technical solution:

An application of a medical cell CMU-pb-7 in preparation of blood lipid-lowering drugs.

A medical cell CMU-pb-7, namely *Lactobacillus rhamnosus* CMU-pb-7, having a collection number of CCTCC NO: M 2022220, has been preserved in China Center for Type Culture Collection (CCTCC), Wuhan University, Wuhan, China, on Mar. 9, 2022, and is named *Lactobacillus rhamnosus* CMU-pb-7 taxonomically.

Further, the medical cell CMU-pb-7 is a bacterial suspension.

Further, an application of the medical cell CMU-pb-7 in preparation of cholesterol-lowering drugs.

Further, an application of the medical cell CMU-pb-7 in preparation of drugs that relieve impaired glucose tolerance caused by a high-fat diet.

Further, an application of the medical cell CMU-pb-7 in preparation of drugs that relieve the fatty change of the liver tissue caused by a high-fat diet.

It can be known from the above technical solution that compared with the prior art, the present invention provides an application of a medical cell CMU-pb-7 in preparation of blood lipid-lowering drugs, and the medical cell CMU-pb-7 is a strain of *Lactobacillus rhamnosus* isolated from feces of healthy people at the early stage in the laboratory, which can relieve impaired glucose tolerance caused by a high-fat diet in mice with hyperlipidemia, reduce the blood lipid level, enhance the antioxidant capacity of the liver tissue, and regulate the expression of key proteins of liver lipid metabolism to relieve fatty change caused by a high-fat diet. The medical cell CMU-pb-7 provided by the present invention has a great potential application prospect in preparation of blood lipid-lowering drugs.

DESCRIPTION OF DRAWINGS

To more clearly describe the technical solution in the embodiments of the present invention or in the prior art, the drawings required to be used in the description of the embodiments or the prior art will be simply presented below. Apparently, the drawings in the following description are merely the embodiments of the present invention, and for those ordinary skilled in the art, other drawings can also be obtained according to the provided drawings without contributing creative labor.

Where, *, $P<0.05$; , $P<0.01$; *, $P<0.001$; ****, $P<0.0001$.

DETAILED DESCRIPTION

The technical solutions in the embodiments of the present invention will be clearly and fully described below in combination with the drawings in the embodiments of the present invention. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

Embodiment 1 Isolation, Cultivation, Identification and Prebiotic Function Test of CMU-pb-7

(1) Sample Source

Healthy people are selected as volunteers. The people selected are required to eat a normal diet for two weeks prior to sampling and have no history of intestinal diseases or antibiotic uses. Feces in the morning of the day are taken as samples. After fresh samples are collected, an intelligent microorganism isolation system of Nanjing FMT medical Co., Ltd. is used for fecal bacteria isolation immediately. After isolation, a crude fecal bacteria solution is collected, added into an MRS broth medium containing 40% of glycerol as a frozen protective solution, and frozen in a $-80°$ C. ultra-low temperature refrigerator for later use.

(2) Isolation of CMU-pb-7

The crude fecal bacteria solution is taken out from the $-80°$ C. refrigerator, and 1 mL of crude fecal bacteria solution is added into 9 mL of normal saline, mixed thoroughly, and gradiently diluted to a concentration of $10^{-3}$ to $10^{-7}$. 100 µL of bacterial solution of each concentration is drawn, respectively applied to an MRS agar medium, a TPY agar medium and an M17 agar medium, and cultured at $37°$ C. in anaerobic conditions for 48 h to 72 h. According to the characteristics of colonies, single colonies with a round shape, a smooth surface, a neat edge, a creamy white color and a creamy flavor are selected for pure culture on corresponding agar media.

(3) Cultural Characteristics of CMU-pb-7

Figure 1:
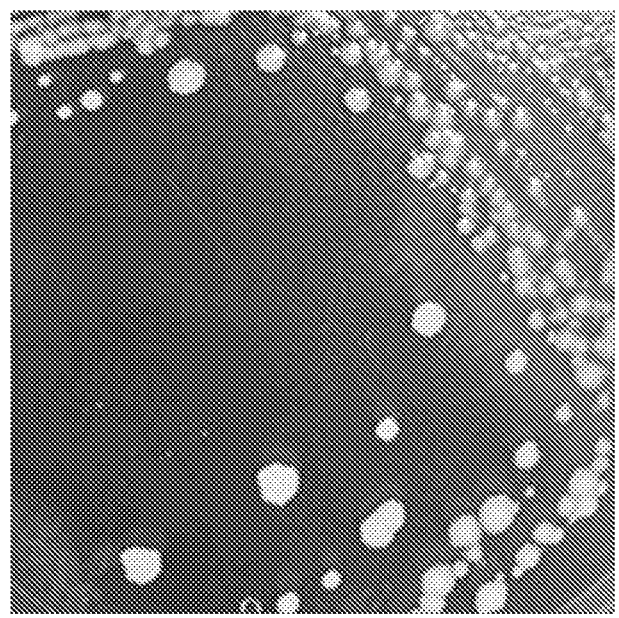
FIG. 1 is colony morphology of a medical cell CMU-pb-7 of the present invention on an MRS agar plate.
Figure 2:
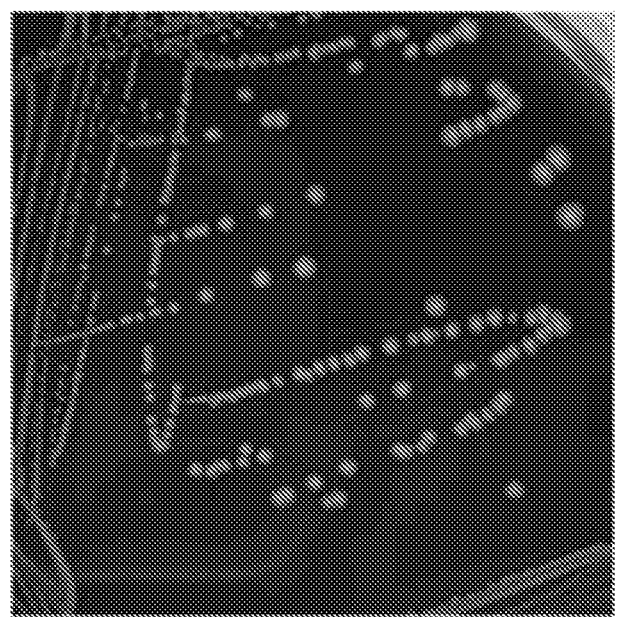
FIG. 2 is colony morphology of a medical cell CMU-pb-7 of the present invention on an anaerobic blood agar plate.

The single colonies of a CMU-pb-7 strain are respectively inoculated on an MRS agar plate and an anaerobic blood agar plate, and cultured at $37°$ C. in anaerobic conditions for 48 h; the characteristics of the colonies on the MRS plate and the anaerobic blood agar plate are observed, and the results are shown in FIG. 1 to FIG. 2, which show that CMU-pb-7 is a facultative anaerobe, the colonies on the MRS plate and the anaerobic blood agar plate have a round shape, a smooth surface, a neat edge, a creamy white color and a creamy flavor, and no hemolysis is observed on the anaerobic blood agar plate.

(4) Biochemical Identification of CMU-pb-7

Biochemical identification of CMU-pb-7 is carried out by an API 50CHL bacterial biochemical identification system of BioMérieux. Operations are carried out strictly according to the instructions of API 50CHL identification reagent strips, and the reaction results of the strain are obtained and analyzed by API identification software. The identification results show that the strain is *Lactobacillus rhamnosus*, with an identification rate of 99.9% and a T value of 0.3. The biochemical reaction results of CMU-pb-7 are shown in Table 1.

Table 1 Biochemical Reaction Results of CMU-pb-7

TABLE 1

Carbohydrate utilization of the *Lactobacillus rhamnosus* strain by using API 50CHL

| No. | Substrate | 24 h Reaction | 48 h Reaction |
|---|---|---|---|
| 0 | 0 | − | − |
| 1 | GLY | − | − |
| 2 | ERY | − | − |
| 3 | DARA | − | − |
| 4 | LARA | − | − |
| 5 | RIB | + | + |
| 6 | DXYL | − | − |
| 7 | LXYL | − | − |
| 8 | ADO | − | − |
| 9 | MDX | − | − |
| 10 | GAL | + | + |
| 11 | GLU | + | + |
| 12 | FRU | + | + |
| 13 | MNE | + | + |
| 14 | SBE | + | + |

TABLE 1-continued

Carbohydrate utilization of the *Lactobacillus rhamnosus* strain by using API 50CHL

| No. | Substrate | 24 h Reaction | 48 h Reaction |
|---|---|---|---|
| 15 | RHA | − | + |
| 16 | DUL | − | + |
| 17 | INO | − | − |
| 18 | MAN | + | + |
| 19 | SOR | + | + |
| 20 | MDM | − | − |
| 21 | MDG | + | + |
| 22 | NAG | + | + |
| 23 | AMY | + | + |
| 24 | ARB | + | + |
| 25 | ESC | + | + |
| 26 | SAL | + | + |
| 27 | CEL | + | + |
| 28 | MAL | − | + |
| 29 | LAC | + | + |
| 30 | MEL | − | − |
| 31 | SAC | − | − |
| 32 | TRE | + | + |
| 33 | INU | − | − |
| 34 | MLZ | + | + |
| 35 | RAF | − | − |
| 36 | AMD | − | − |
| 37 | GLYG | − | − |
| 38 | XLT | − | − |
| 39 | GEN | − | + |
| 40 | TUR | − | − |
| 41 | LYX | − | − |
| 42 | TAG | + | + |
| 43 | DFUC | − | − |
| 44 | LFUC | − | + |
| 45 | DARL | − | − |
| 46 | LARL | − | − |
| 47 | GNT | − | − |
| 48 | 2KG | − | − |
| 49 | 5KG | + | + |

"+": positive reaction;
"−": negative reaction.

Where, No. 0 tube is a blank control.

(5) Morphology of Gram-Stained Mycelium of CMU-pb-7

Figure 3:
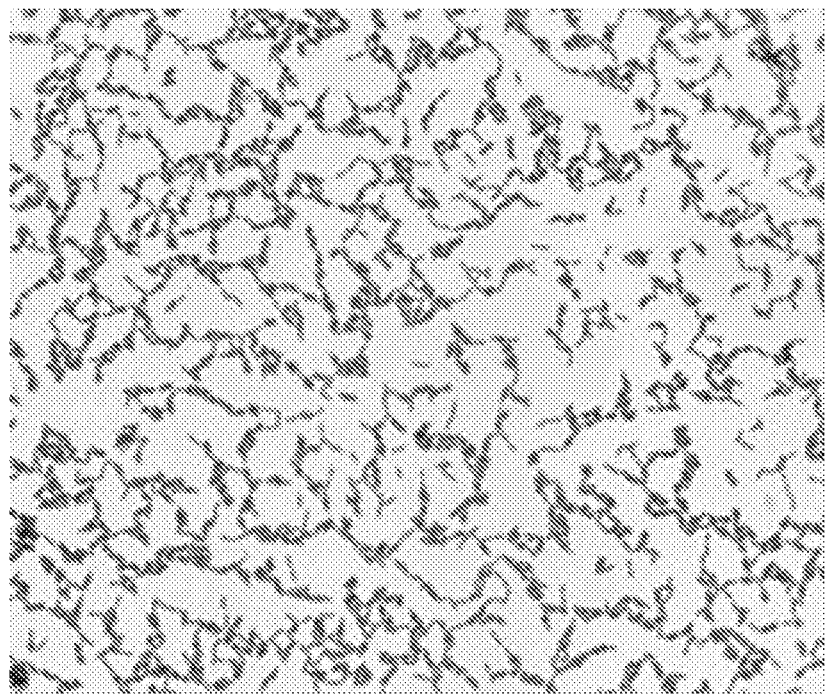
FIG. 3 is morphology of a medical cell CMU-pb-7 of the present invention under a Gram staining microscope (1000×)

The single colony of CMU-pb-7 on the MRS agar plate is selected and smeared on a glass slide containing 10 μL of sterile normal saline; after the glass slide is dried, the external flame of an alcohol lamp is fixed; after the glass slide is cooled, Gram staining is performed, and the morphology of the mycelium is observed under an oil lens; and the results are shown in FIG. 3, which show that CMU-pb-7 is a purple rod-shaped Gram-positive bacterium arranged singly, in pairs or in short chains.

(6) Biofilm Formation Experiment of CMU-pb-7

Figure 4:
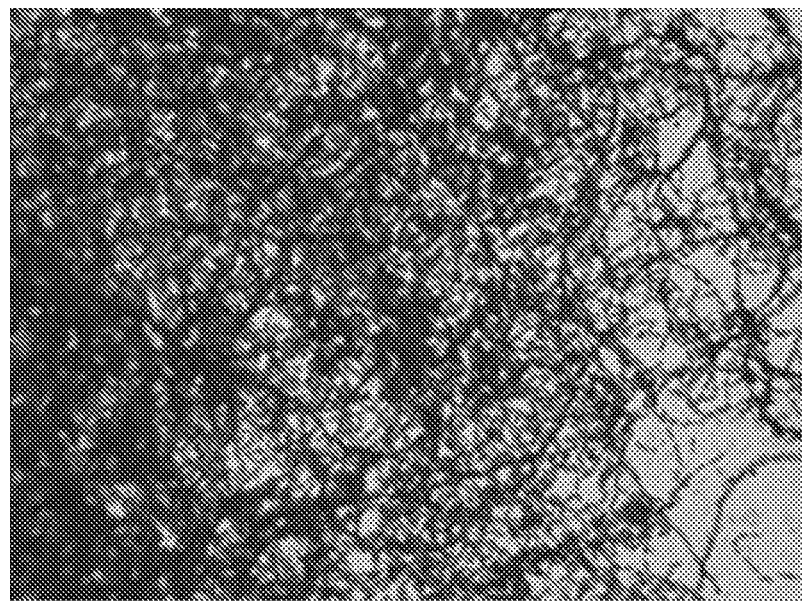
FIG. 4 is a biofilm formation diagram of a medical cell CMU-pb-7 of the present invention (1000×)

$1 \times 10^9$ CFU/mL CMU-pb-7 bacteria solution is inoculated into 15 mL of MRS broth medium at an inoculation rate of 2% (v/v), mixed thoroughly, added into a 6-well plate petri dish with cell slides placed in advance at an amount of 2 mL of bacteria solution per well, and cultured at 37° C. in anaerobic conditions for 72 h. After the culture is completed, the medium is discarded, and the cell slides are taken out, washed with sterile PBS for 3 times, and fixed with 2.5% glutaraldehyde for 6 h to 8 h. After the fixation is completed, the cell slides are washed with sterile PBS for 3 times, and dyed with 1% crystal violet staining solution for 30 min. After the dying is completed, the cell slides are washed with sterile PBS for 3 times. After the cell slides are dried, the biofilm formation is observed under an oil lens. The results are shown in FIG. 4, which show that CMU-pb-7 has the ability of biofilm formation and the morphology of the biofilm presents chain-like aggregation and arrangement.

(7) Cholesterol-Lowering Ability Test of CMU-pb-7

Figure 5:
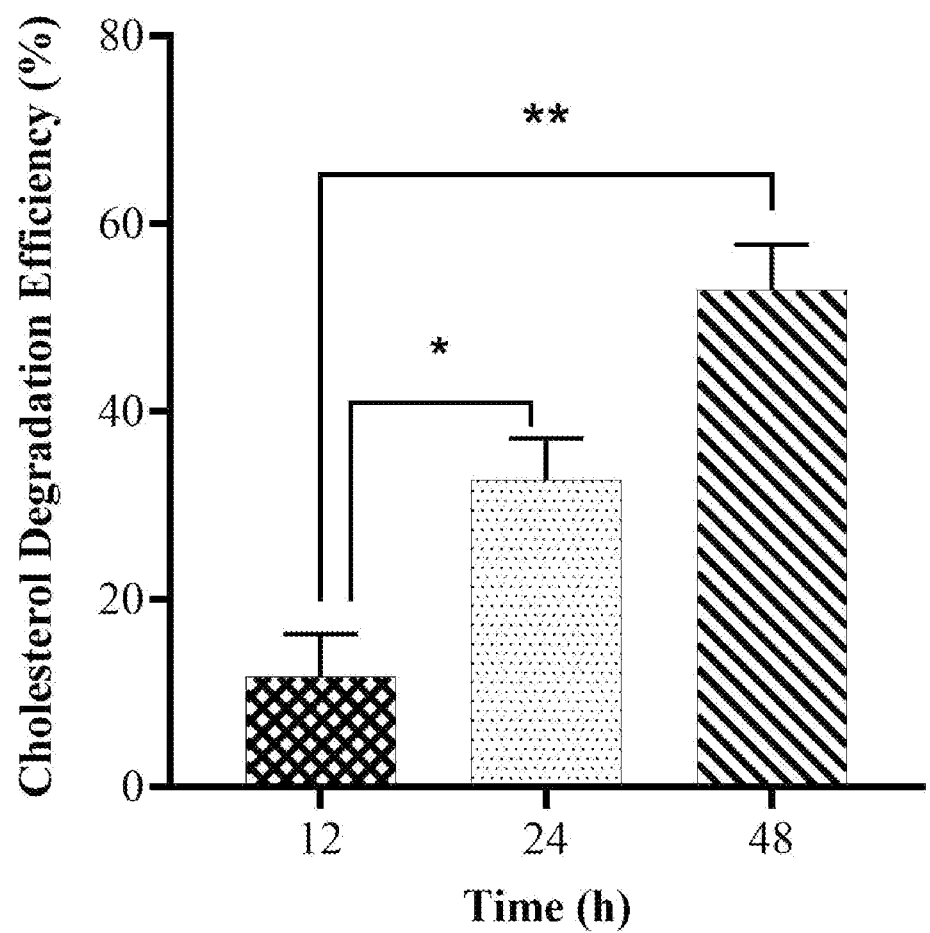
FIG. 5 shows results of in vitro cholesterol degradation rate of a medical cell CMU-pb-7 of the present invention.

$1 \times 10^9$ CFU/mL CMU-pb-7 bacteria solution is respectively inoculated into 10 mL of MRS broth medium with high cholesterol (a standard cholesterol reserve solution (10.0 g/L) is prepared first: 0.1 g of cholesterol (Sigma company) is dissolved with anhydrous ethanol to 10 mL to obtain the concentration of 10.0 g/L, filtered with a 0.22 μm filter membrane to remove bacteria, and stored in a dry sterile centrifuge tube. MRS broth medium with high cholesterol (1 g/L): 1 mL of standard cholesterol reserve solution is added into 9 mL of sterilized MRS broth medium (Guangdong Huankai Microbial Sci.&Tech. Co., Ltd.) to obtain the final concentration of 1 g/L.) and 10 mL of MRS broth medium at an inoculation rate of 2% (v/v), and cultured at 37° C. in anaerobic conditions for 0 h, 12 h, 24 h and 48 h respectively, and 1 mL is sampled and centrifuged at 4000 r/min for 10 min. With the supernatant obtained after inoculation to the MRS broth medium with high cholesterol and centrifugation as a sample to be tested, the supernatant obtained after inoculation to the MRS broth medium and centrifugation as a blank control and the standard solution (5 mmol/L) in a total cholesterol kit (manufacturer: Applygen Technologies Inc., article No.: E1015-50) as a standard, determination is carried out according to the operation steps in the instructions of the kit: 190 μl of working solution (which is prepared at a ratio of 4:1, i.e., 4 mL of reagent R1 is mixed with 1 mL of reagent R2 for immediate use or storage at 4° C.) is added into a 96-well plate, and 10 μl of blank control, 10 μl of standard and 10 μl of sample to be tested are respectively added into each working solution. The OD550 nm value of each tube is determined by a microplate reader after reaction at room temperature of 37° C. for 20 min. Cholesterol content (mmol/L)=[(sample well OD550 nm−blank well OD550 nm)/(standard well OD550 nm−blank well OD550 nm)]×$C_{standard}$, wherein OD550 nm is the absorbance value measured by the microplate reader with the working wavelength of 550 nm, and the $C_{standard}$ is the concentration 5 mmol/L of the standard solution. The cholesterol degradation efficiency is calculated according to the following formula: cholesterol degradation rate %=(C0−Cn)/C0×100%, wherein C0 is the cholesterol content in the MRS-CHO medium before culture, and Cn is the cholesterol content in the medium of an experimental strain at different time points. The results are shown in FIG. 5, which show that with the extension of the culture time, the cholesterol degradation rate of CMU-pb-7 is increased gradually and can reach 52.93% at 48 h.

Embodiment 2 Establishment of Mouse Model of Hyperlipidemia

24 SPF grade male C57BL/6 mice aged 6 to 8 weeks and weighing 19 to 21 g are selected. The mice are randomly divided into 3 groups with 8 mice in each group, which are respectively a control group (normal diet, ND): treated by gavage with a normal diet (manufacturer: Beijing Keao Xieli Feed Co., Ltd., name: Growth and Reproduction Feed for Rats and Mice)+0.2 mL of normal saline; a model group (high-fat diet, HFD): treated by gavage with a high-fat diet (manufacturer: Jiangsu Xietong Pharmaceutical Bio-engineering Co., Ltd., name: 60% Kcal High Fat Diet, article No.: XTHF60)+0.2 mL of normal saline; and a HFD+CMU-pb-7 group: treated by gavage with a high-fat diet +0.2 mL of 1×109 CFU/mL CMU-pb-7. Each group of mice are treated by gavage at a fixed time every day. The mice are treated for 9 continuous weeks, and executed by cervical dislocation after eyeball blood collection. Samples of the blood, liver and ileum of the mice are reserved for later detection and analysis.

Figure 6:
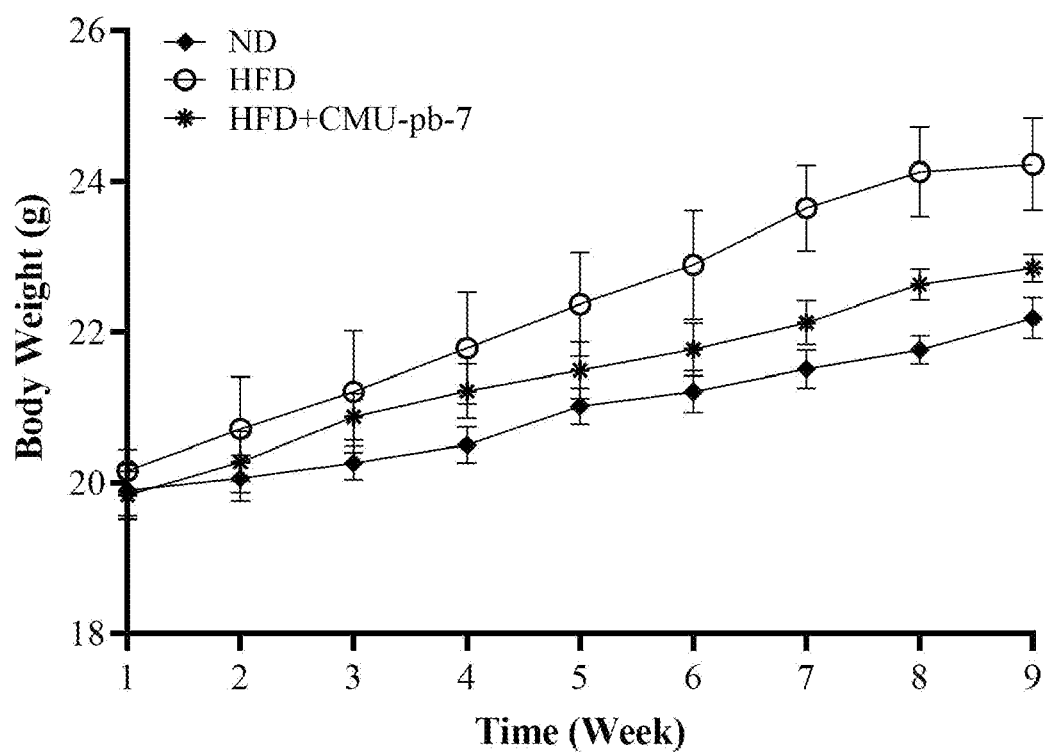
FIG. 6 shows the weight growth change of a mouse model of hyperlipidemia with a medical cell CMU-pb-7 of the present invention.
Figure 7:
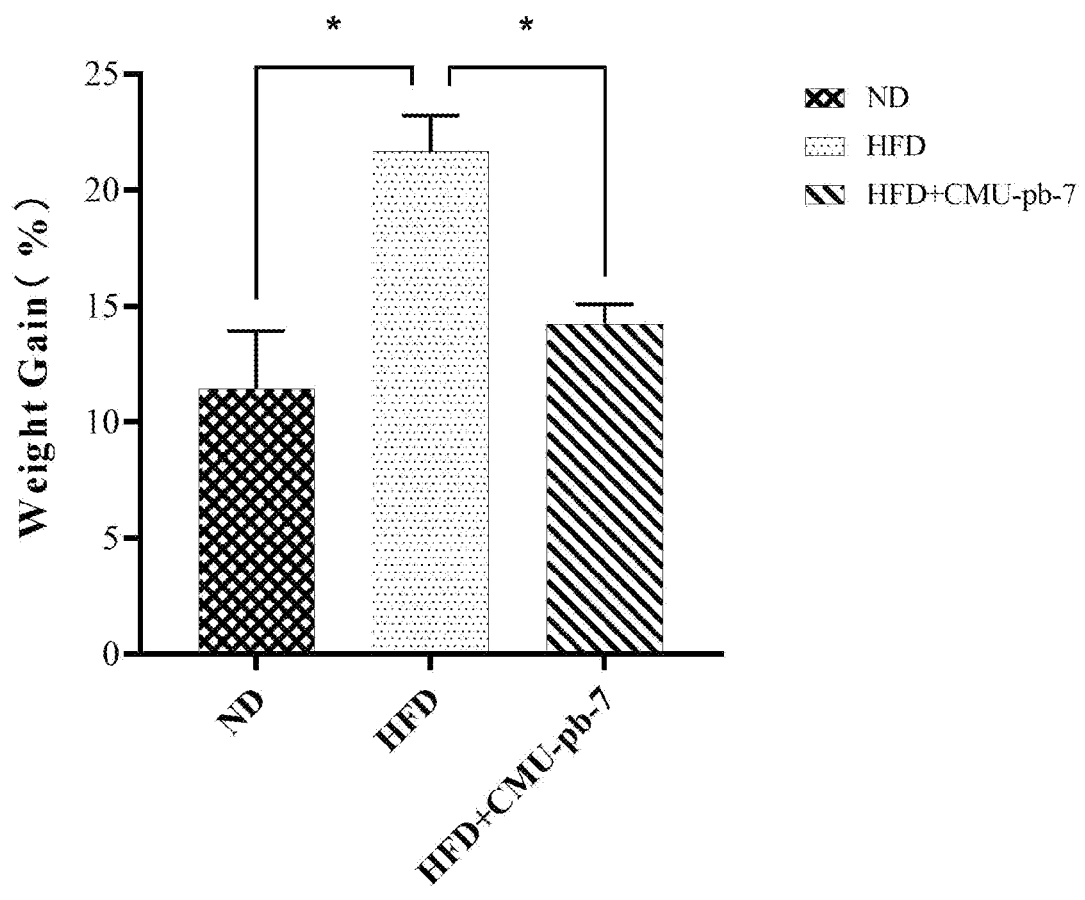
FIG. 7 shows changes in the weight growth rate of a mouse model of hyperlipidemia with a medical cell CMU-pb-7 of the present invention.

Embodiment 3 Assessment of Mouse Model of Hyperlipidemia (1) Detection of Influence of CMU-pb-7 Medical Cell on Weight of Mice with Hyperlipidemia Each mouse is weighed on an electronic balance at a fixed time before gavage. The results of the weight change and weight growth rate of the mice (the weight of mice in week 9–the weight of mice in week 1)/the weight of mice in week 1) are shown in FIG. 6 and FIG. 7, which show that after gavage for 9 continuous weeks, the weight of the mice in the HFD+CMU-pb-7 group is lower than that in the HFD group and higher than that in the ND group at each time point. Meanwhile, the weight growth rate of the mice in the HFD+CMU-pb-7 group is significantly lower than that in the HFD group ($P<0.05$), and has no significant change from that of the mice in the ND group.

(2) Glucose Tolerance Test of Mice with Hyperlipidemia

Figure 8:
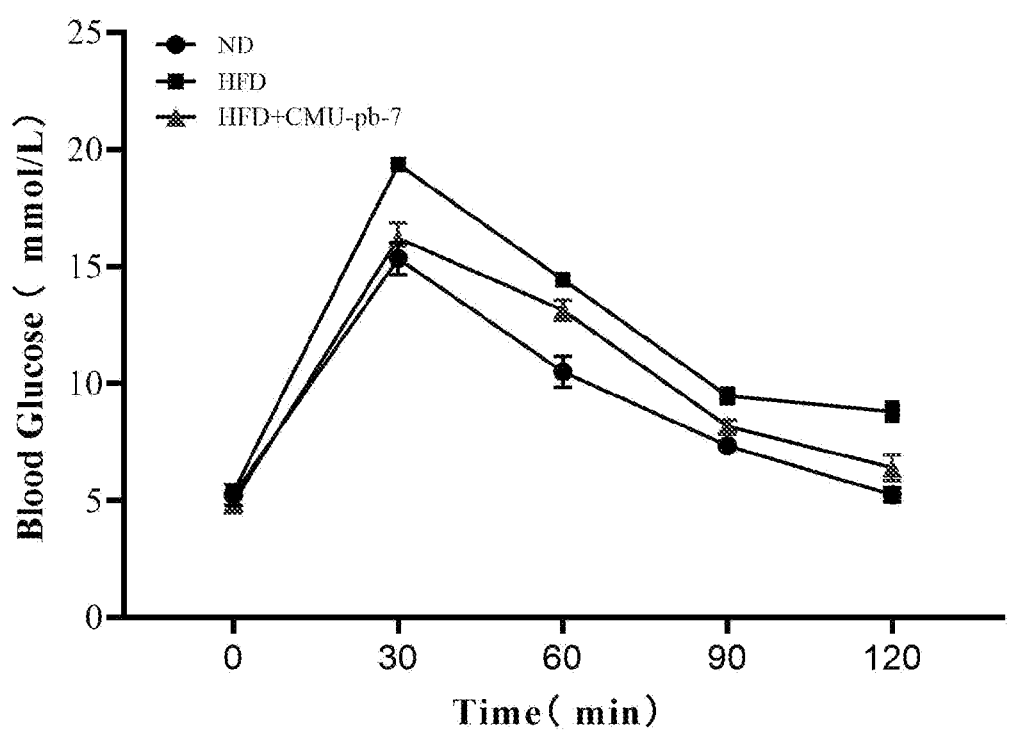
FIG. 8 shows glucose tolerance detection results of a mouse model of hyperlipidemia with a medical cell CMU-pb-7 of the present invention.
Figure 9:
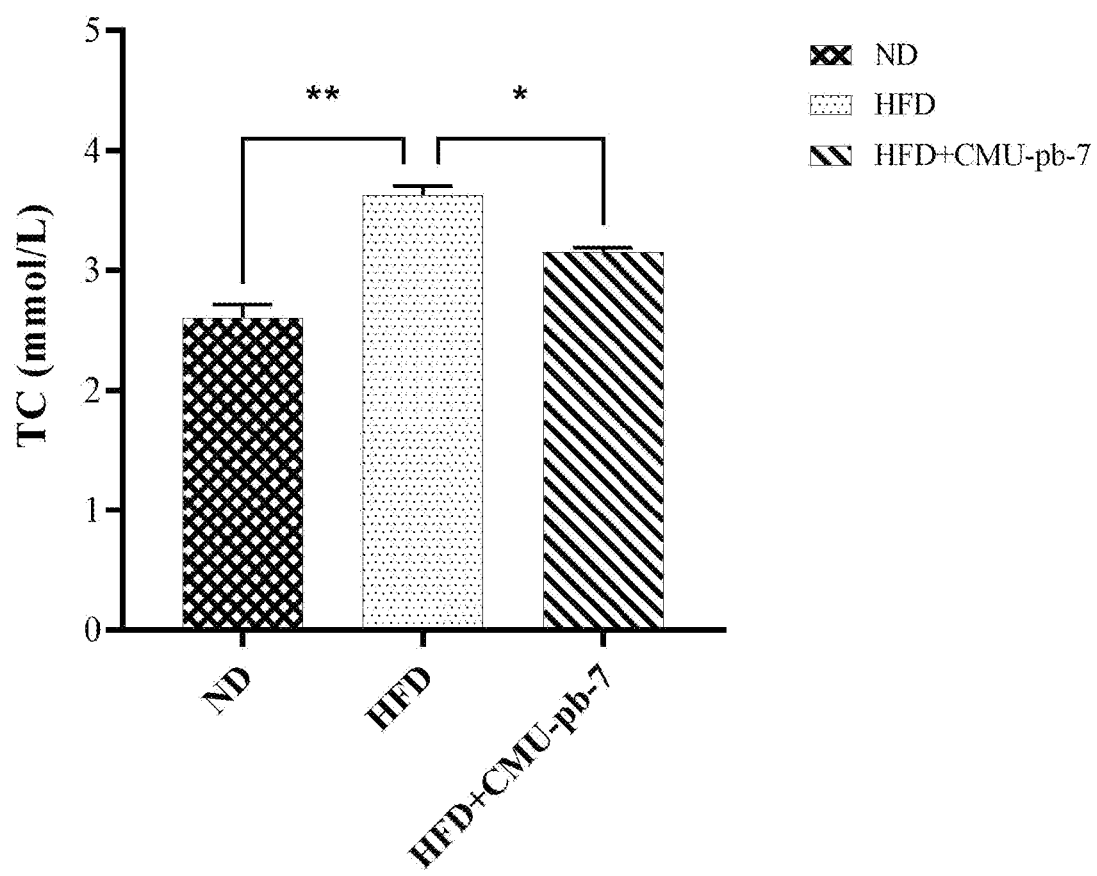
FIG. 9 shows serum TC level detection results of a mouse model of hyperlipidemia with a medical cell CMU-pb-7 of the present invention.
Figure 10:
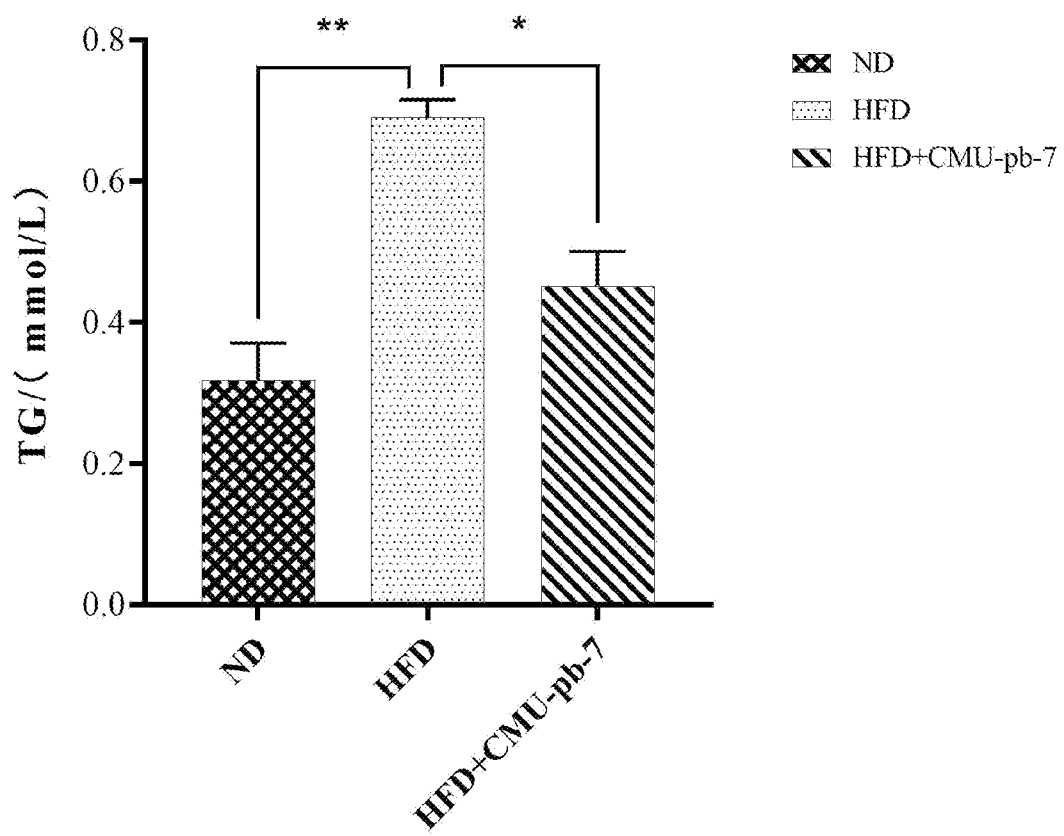
FIG. 10 shows serum TG level detection results of a mouse model of hyperlipidemia with a medical cell CMU-pb-7 of the present invention.
Figure 11:
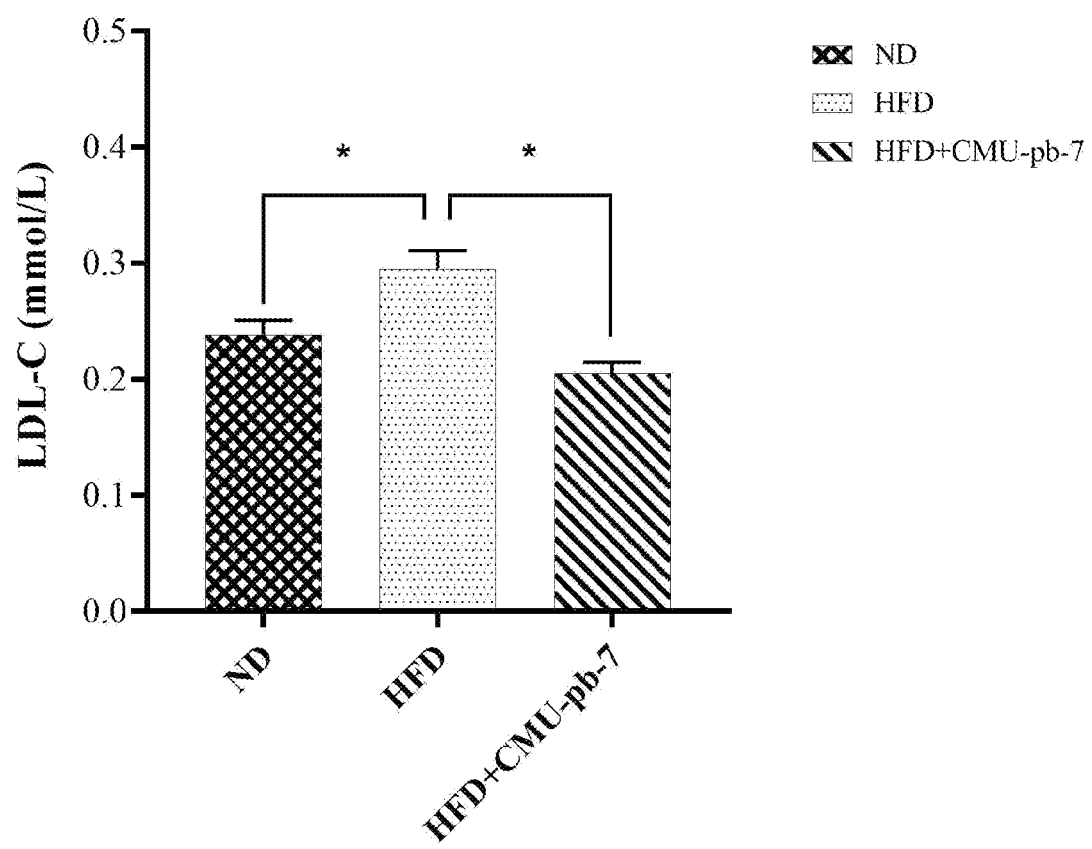
FIG. 11 shows serum LDL-C level detection results of a mouse model of hyperlipidemia with a medical cell CMU-pb-7 of the present invention.
Figure 12:
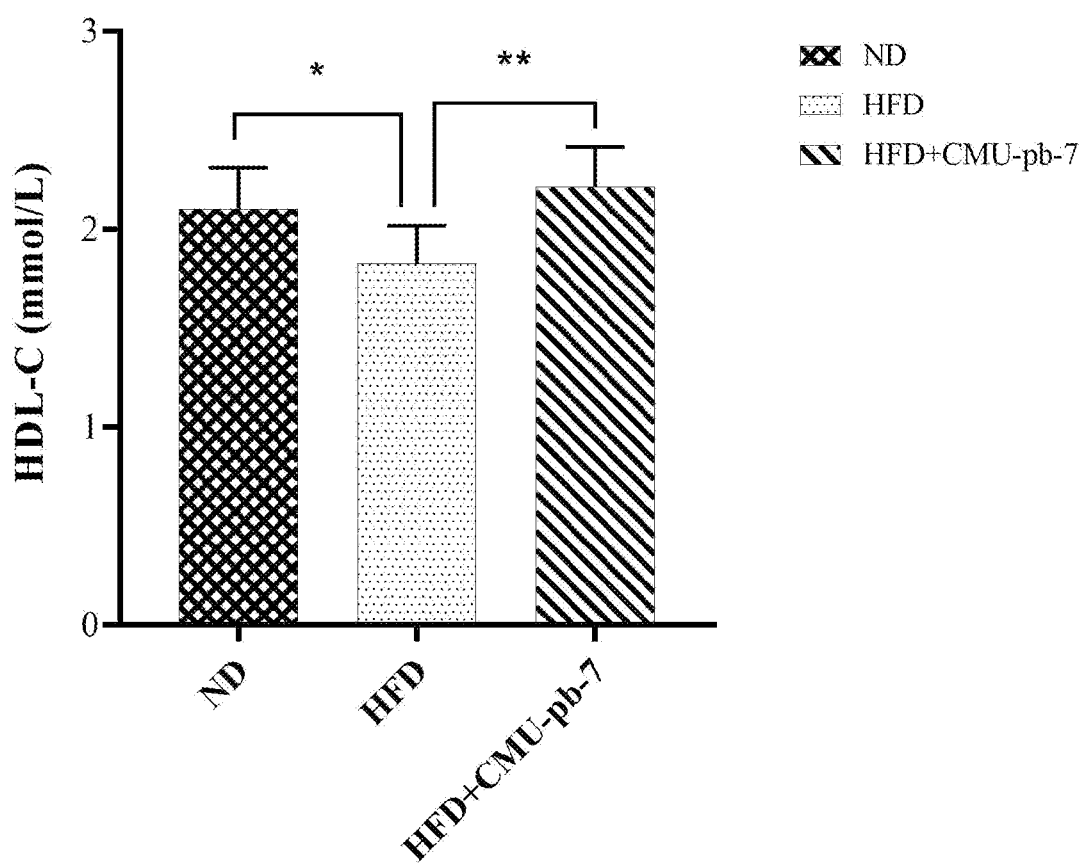
FIG. 12 shows serum HDL-C level detection results of a mouse model of hyperlipidemia with a medical cell CMU-pb-7 of the present invention.
Figure 13:
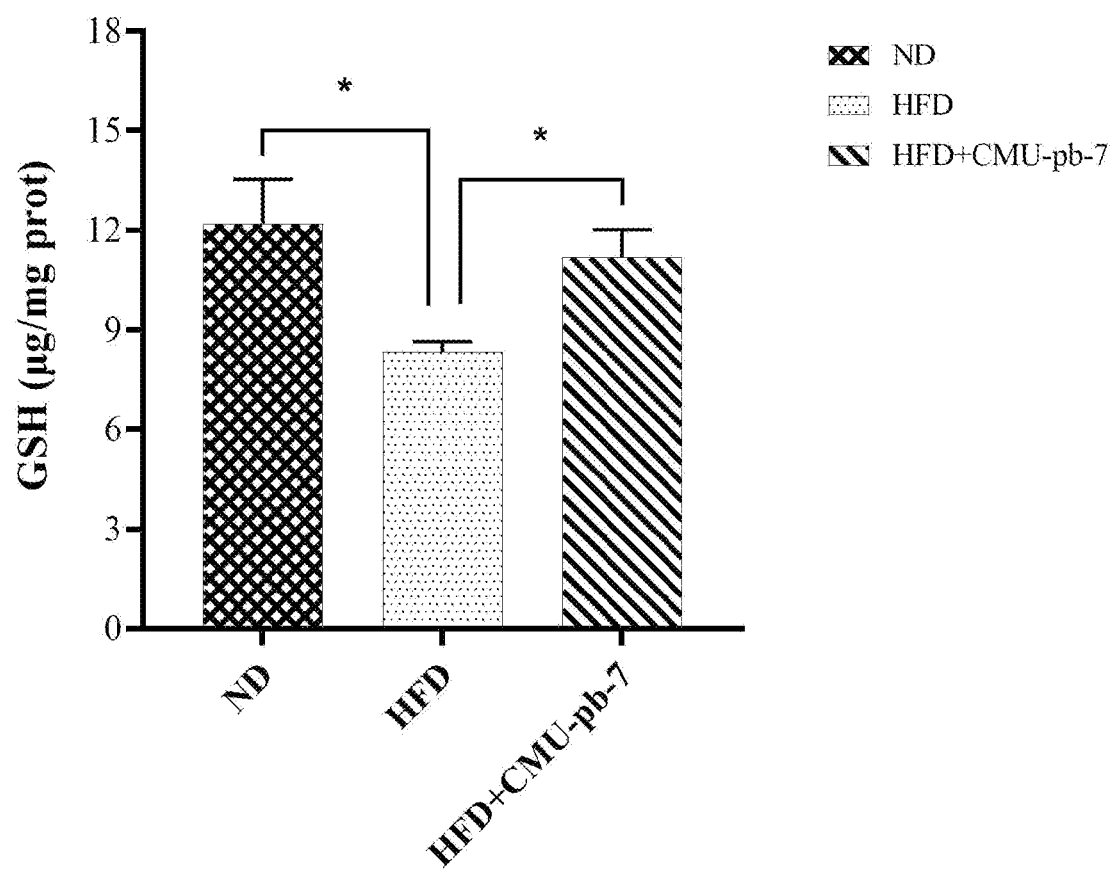
FIG. 13 shows GSH level detection results of a mouse model of hyperlipidemia with a medical cell CMU-pb-7 of the present invention.
Figure 14:
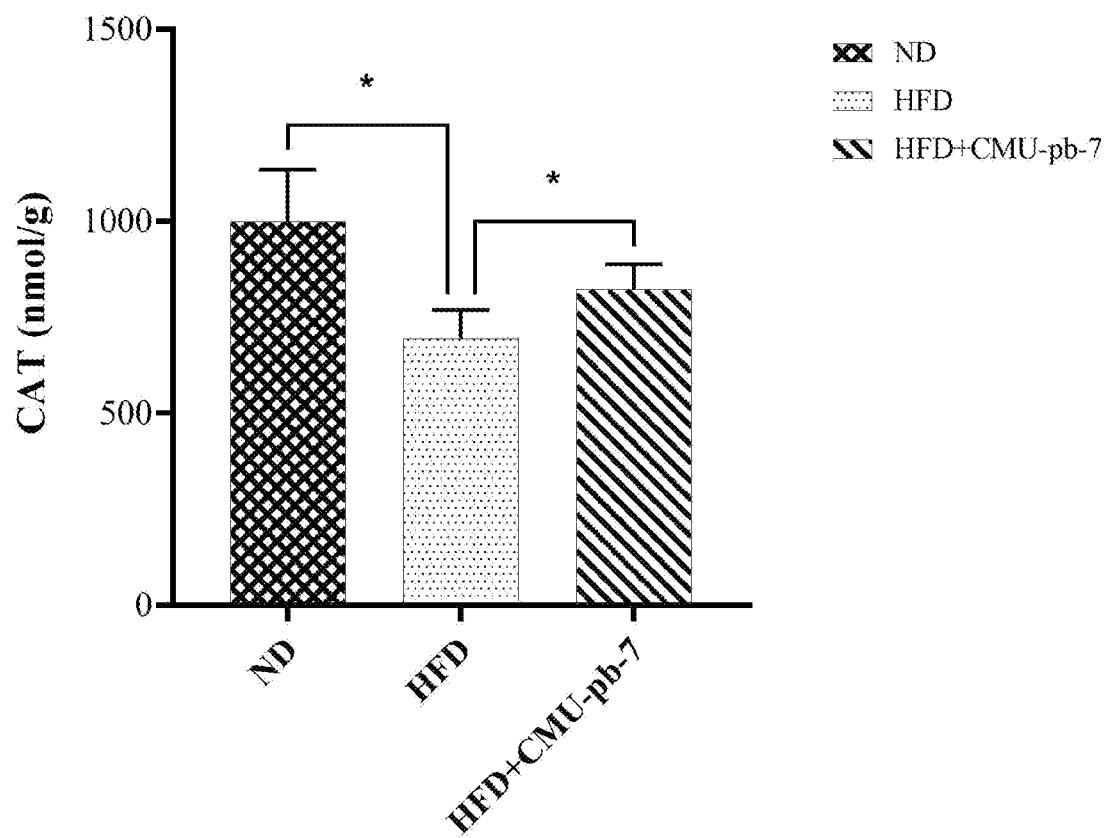
FIG. 14 shows CAT level detection results of a mouse model of hyperlipidemia with a medical cell CMU-pb-7 of the present invention.
Figure 15:
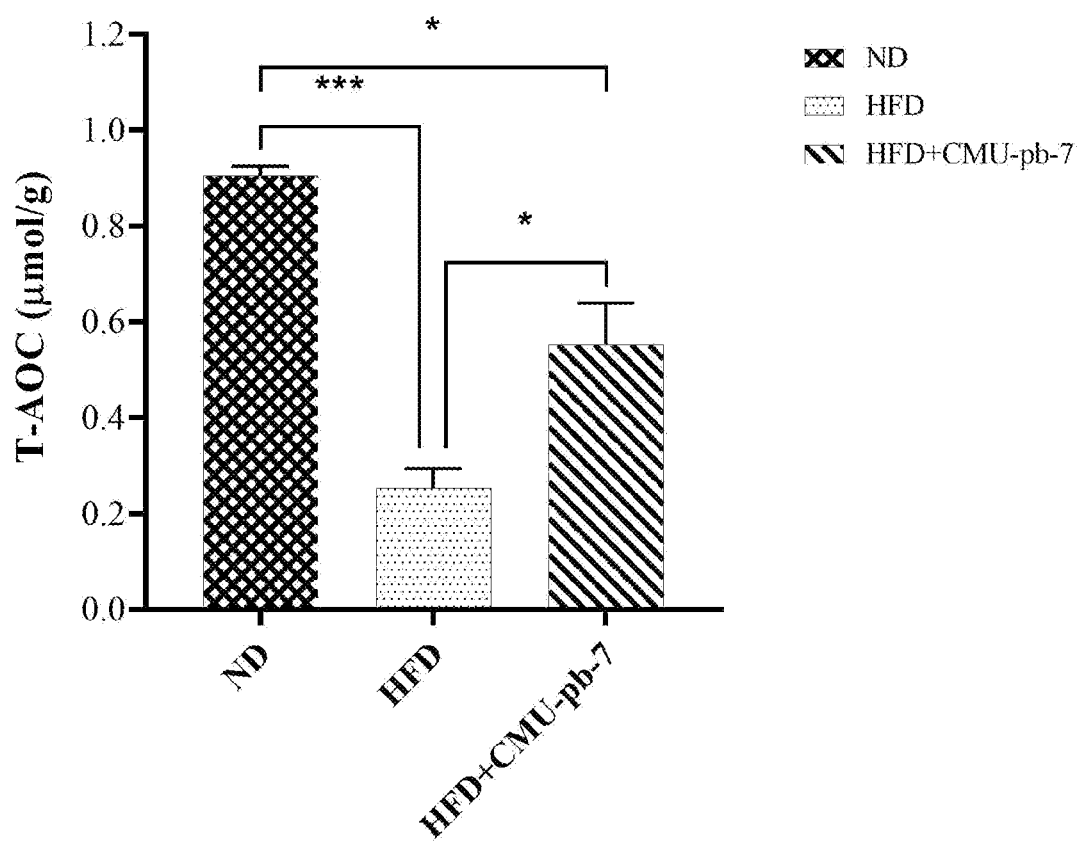
FIG. 15 shows T-AOC level detection results of a mouse model of hyperlipidemia with a medical cell CMU-pb-7 of the present invention.
Figure 16:
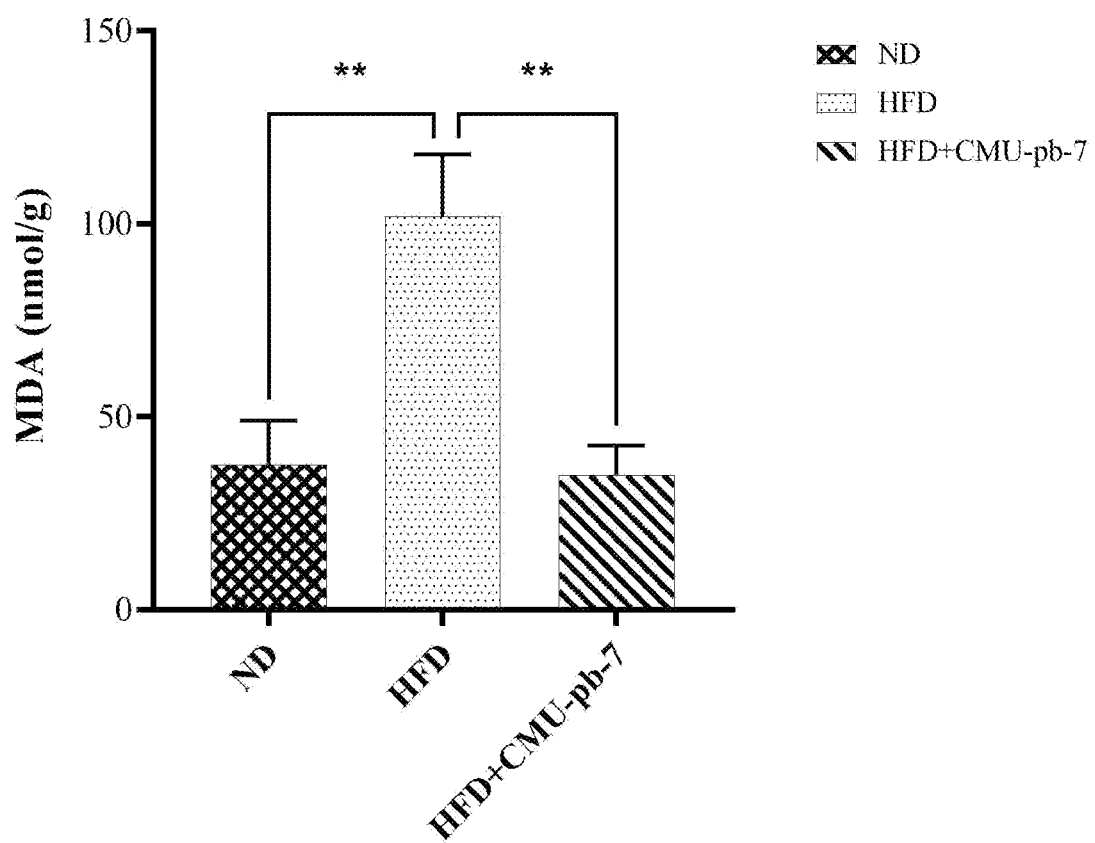
FIG. 16 shows MDA level detection results of a mouse model of hyperlipidemia with a medical cell CMU-pb-7 of the present invention.

On the last night of gavage for 9 continuous weeks, the mice are deprived of food but not water. At 8 o'clock the next day, the fasting blood glucose of each mouse is measured with a glucose meter. After the measurement of fasting blood glucose, each mouse is intraperitoneally injected with 20% glucose solution at 0.01 mL/g (the amount of glucose used in the glucose tolerance test of mice is 2 g/kg, and PBS is used to prepare 20% glucose solution), and the blood glucose of the mice is measured at time points of 30 min, 60 min, 90 min and 120 min. The results are shown in FIG. 8, which show that the blood glucose concentration of the mice in each group is increased to the highest point at 30 min and gradually decreased at 60 min, 90 min and 120 min. Compared with the HFD group, the blood glucose level of the mice in the ND group is decreased, indicating that a high-fat diet results in impaired glucose tolerance of the mice; and the blood glucose level of the mice in the HFD+CMU-pb-7 group is lower than that in the HFD group but higher than that in the ND group at each time point, indicating that CMU-pb-7 can relieve the impaired glucose tolerance of the mice caused by a high-fat diet.

(3) Blood Lipid Test of Mice with Hyperlipidemia

The serum of the mice is collected by means of eyeball blood collection and centrifuged in a 4° C. refrigerated centrifuge at 2000 r/min for 15 min, the supernatant is collected, and the levels of total cholesterol (TC), triglycerides (TG), high-density lipoprotein cholesterol (HDL-C) and low-density lipoprotein cholesterol (LDL-C) are determined with an automatic biochemical analyzer (Mindray). The results are shown in FIG. 9 to FIG. 12, which show that the serum TC, TG and LDL-C levels of the mice in the HFD group are higher than those in the ND group ($P<0.05$), indicating that a mouse model of hyperlipidemia is established successfully; and compared with the HFD group, the serum TC, TG and LDL-C levels of the mice in the HFD+CMU-pb-7 group are decreased, while the HDL-C level is increased ($P<0.05$), indicating that CMU-pb-7 can regulate the blood lipid level of mice with hyperlipidemia to a certain extent.

(4) Liver Antioxidant Factor Detection of Mice with Hyperlipidemia 0.1 g of mouse liver tissue is added into 1 mL of precooled lysate (Solarbio), homogenized and centrifuged at 10000 r/min at 4° C. for 5 min; and the supernatant is collected. The levels of antioxidant factors in the liver tissue are respectively determined by a reductive glutathione (GSH) assay kit, a hydrogen peroxide (CAT) activity assay kit and a total antioxidant capacity (T-AOC) assay kit, and the level of lipid peroxidation in the liver tissue is determined by a malondialdehyde (MDA) assay kit. The results are shown in FIG. 13 to FIG. 16, which show that: compared with the ND group, the T-AOC, GSH and CAT levels in the liver of the HFD group are significantly decreased, while the MDA level is increased ($P<0.05$), indicating that the antioxidant capacity of the liver tissue is decreased; and compared with the HFD group, the GSH, CAT and T-AOC levels in the HFD+CMU-pb-7 group are significantly increased, while the MDA level is decreased ($P<0.05$), indicating that CMU-pb-7 can improve the antioxidant capacity of the liver tissue and reduce the oxidative stress level.

(5) Liver Morphological Observation of Mice with Hyperlipidemia

Figure 17:
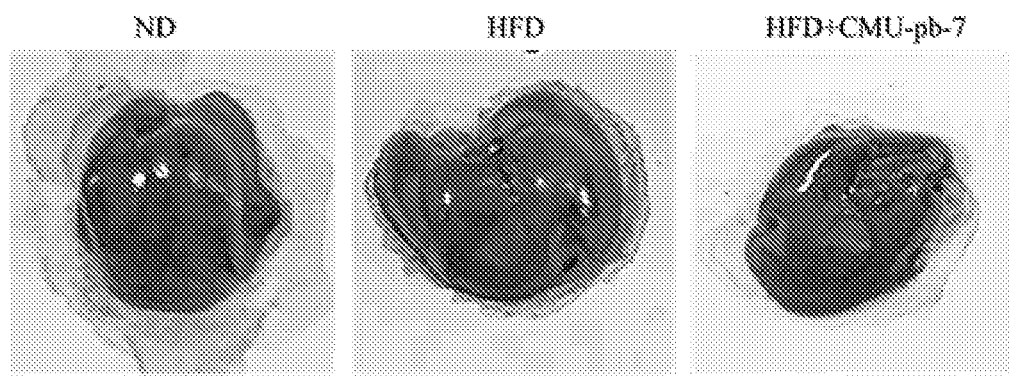
FIG. 17 shows liver tissue morphological observation results of a mouse model of hyperlipidemia with a medical cell CMU-pb-7 of the present invention.

After each mouse is dissected, the liver is rinsed with PBS, and the volume, hardness, smoothness and fatty change of the liver of the mice are observed by naked eyes and recorded by taking photographs. The results are shown in FIG. 17, which show that: compared with the ND group, the volume of the liver of the mice in the HFD group is larger, the texture is hard, the cut surface is greasy, and fatty change is observed; and compared with the HFD group, the volume of the liver of the mice in the HFD+CMU-pb-7 group is smaller, the texture is soft, the cut surface is smooth, and no fatty change is observed, indicating that CMU-pb-7 can improve the antioxidant capacity of the liver tissue and relieve fatty change.

(6) Liver Tissue HE Staining of Mice with Hyperlipidemia

Figure 18:
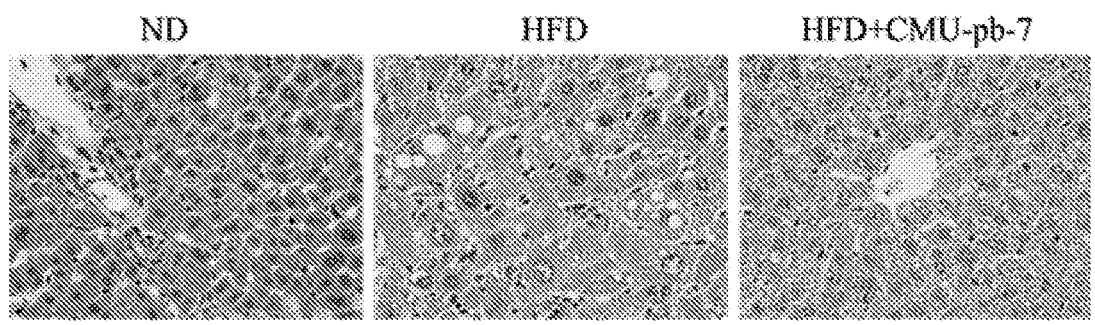
FIG. 18 shows liver tissue pathological section HE staining results of a mouse model of hyperlipidemia with a medical cell CMU-pb-7 of the present invention.

① The liver tissue of the mice in each group is fixed with 4% formaldehyde solution, embedded in paraffin and sliced. ② The paraffin slices are placed in an oven at 60° C. for 1 h and soaked in xylene for 5 min; soaked in anhydrous ethanol, 95% ethanol, 85% ethanol and 75% ethanol for 3 min respectively; and then rinsed with running water and spin-dried. ③ After stained by hematoxylin for 5 min, the paraffin slices are rinsed with running water, differentiated by 1% hydrochloric acid alcohol, and rinsed again with running water; stained by eosin for 1 min; and then soaked in 75% ethanol, 85% ethanol, 95% ethanol and anhydrous ethanol for 1 min respectively, placed in an oven at 60° C. for 5 min, and mounted with neutral resin. ④ Observation is made under a microscope and photographs are taken. The histopathological changes of the liver tissue of the mice in each group are observed and compared under an optical microscope. The results are shown in FIG. 18, which show that: the structure of the liver tissue of the mice in the ND group is normal; the liver cells in the liver tissue of the mice in the HFD group have irregular shapes, disorder in arrangement, rough and loose nuclei, and a large number of lipid droplets, and present obvious fatty change; and the liver cells in the liver tissue of the mice in the HFD+CMU-pb-7 group have regular shapes, orderly arrangement, compact nuclei and a small number of lipid droplets, and present fatty alleviation, which show that CMU-pb-7 can relieve the fatty change of the liver tissue of mice with hyperlipidemia.

(7) Ileum Tissue HE Staining of Mice with Hyperlipidemia

Figure 19:
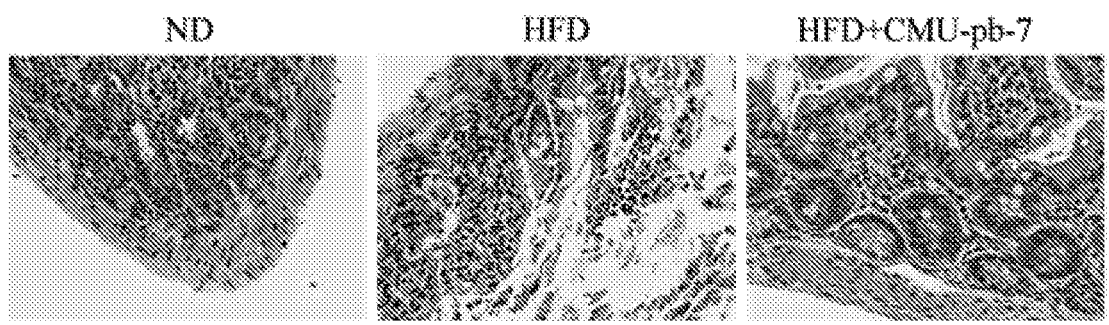
FIG. 19 shows ileum tissue pathological section HE staining results of a mouse model of hyperlipidemia with a medical cell CMU-pb-7 of the present invention.

① The ileum tissue of the mice in each group is fixed with 4% formaldehyde solution, embedded in paraffin and sliced. ② The paraffin slices are placed in an oven at 60° C. for 1 h and soaked in xylene for 5 min; soaked in anhydrous ethanol, 95% ethanol, 85% ethanol and 75% ethanol for 3 min respectively; and then rinsed with running water and spin-dried. ③ After stained by hematoxylin for 5 min, the paraffin slices are rinsed with running water, differentiated by 1% hydrochloric acid alcohol, and rinsed again with running water; stained by eosin for 1 min; and then soaked in 75% ethanol, 85% ethanol, 95% ethanol and anhydrous ethanol for 1 min respectively, placed in an oven at 60° C. for 5 min, and mounted with neutral resin. ④ Observation is made under a microscope and photographs are taken. The histopathological changes of the ileum tissue of the mice in each group are observed and compared under an optical microscope, and the results are shown in FIG. 19, which show that: the structure of the ileum tissue of the mice in the ND group is complete; the intestinal wall structure of the ileum tissue of the mice in the HFD group is incomplete, intestinal villi are broken and absent, epithelial cells are shed, and the injury of the ileum tissue is serious; the intestinal wall structure of the ileum tissue of the mice in the HFD+CMU-pb-7 group is complete, no intestinal villus is broken or absent, epithelial cells are complete and not shed, and the injury of the ileum tissue is relieved, indicating that CMU-pb-7 can regulate the oxidative stress level in the intestinal tract and relieve the oxidative damage of the ileum tissue.

(8) Liver Index Detection of Mice with Hyperlipidemia

Figure 20:
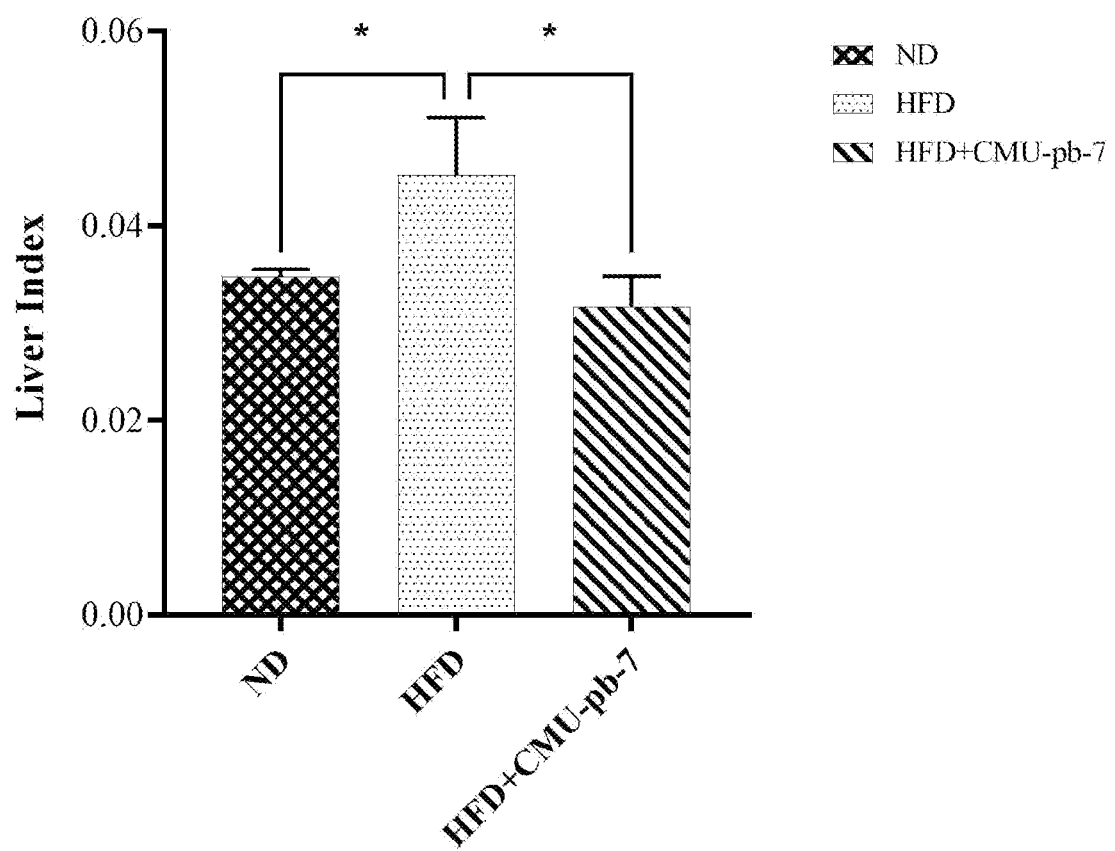
FIG. 20 shows liver index results of a mouse with hyperlipidemia with a medical cell CMU-pb-7 of the present invention.

The mass of each mouse before dissection is denoted as M2, and the mass of the liver tissue of each mouse after dissection is denoted as M1. After weighing, the liver index of each mouse is calculated, and the liver index=M1/M2. The results are shown in FIG. 20, which show that: compared with the ND group, the liver index of the mice in the HFD group is increased (P<0.05); and compared with the HFD group, the liver index of the mice in the HFD+CMU-pb-7 group is decreased (P<0.05), indicating that CMU-pb-7 can relieve the changes of the volume and mass of the liver of the mice.

(9) Liver Histological Injury Scores of Mice with Hyperlipidemia

Figure 21:
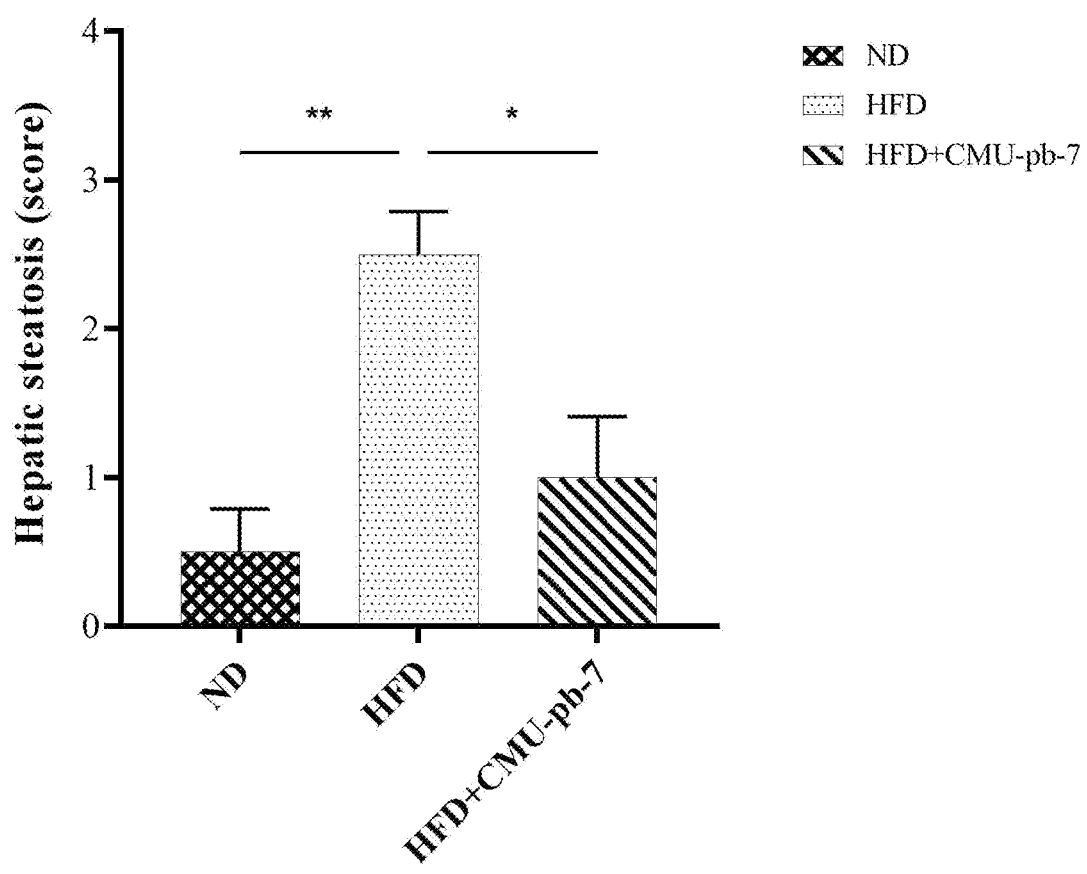
FIG. 21 shows liver histological injury scores of a mouse with hyperlipidemia with a medical cell CMU-pb-7 of the present invention.

Liver histological injury scores: 0: fatty change in less than 5% of liver cells; 1: fatty change in 5%-33% of liver cells; 2: fatty change in 33%-66% of liver cells; and 3: fatty change in more than 66% of liver cells. The assessment results are shown in FIG. 21, which show that: the liver tissue injury scores of the mice in the HFD+CMU-pb-7 group are significantly lower than those in the HFD group, indicating that CMU-pb-7 can relieve the fatty change of the liver tissue of mice with hyperlipidemia.

(10) Ileum Histological Injury Scores of Mice with Hyperlipidemia

Figure 22:
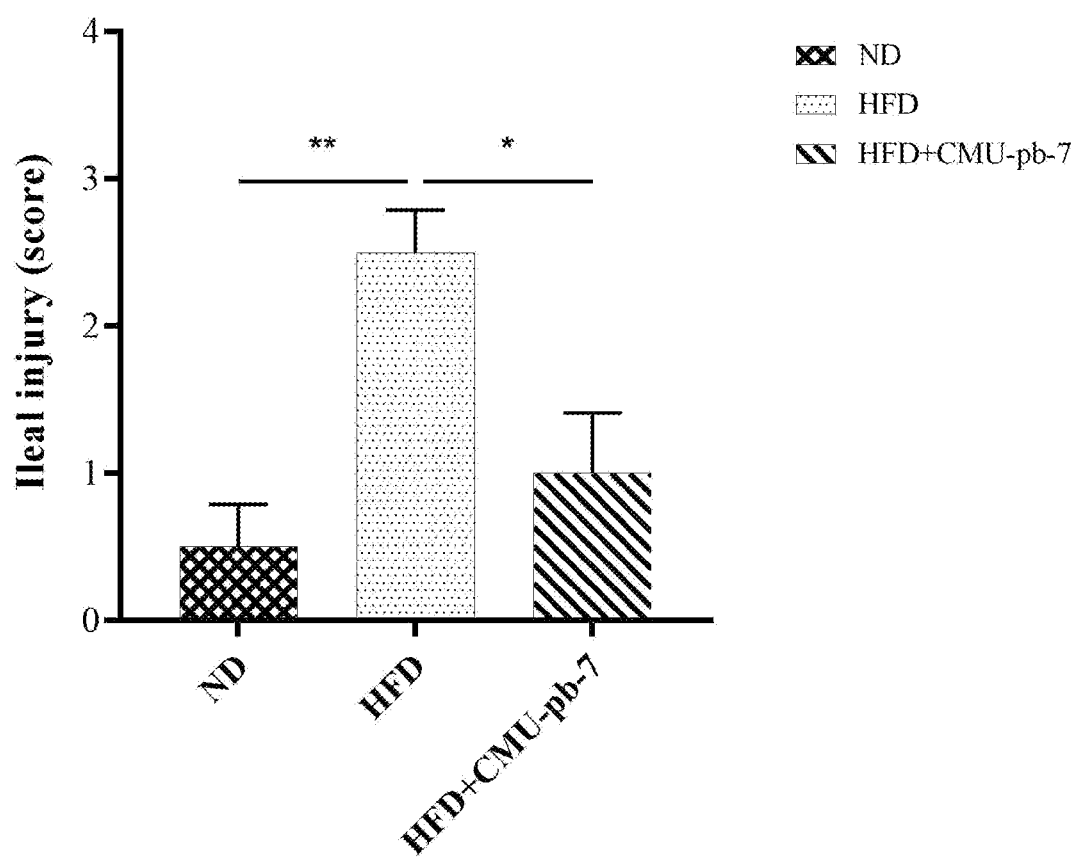
FIG. 22 shows ileum histological injury scores of a mouse with hyperlipidemia with a medical cell CMU-pb-7 of the present invention.
Figure 23:
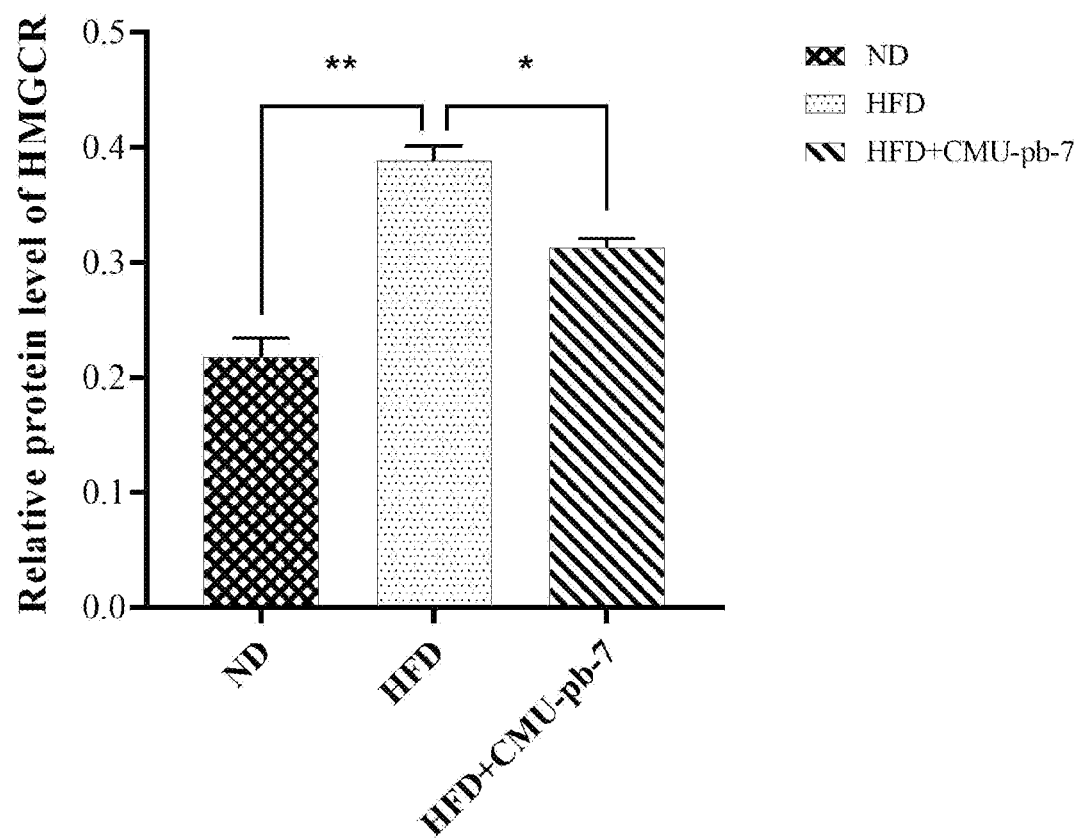
FIG. 23 shows liver HMGCR protein expression level detection results of a mouse with hyperlipidemia with a medical cell CMU-pb-7 of the present invention.
Figure 24:
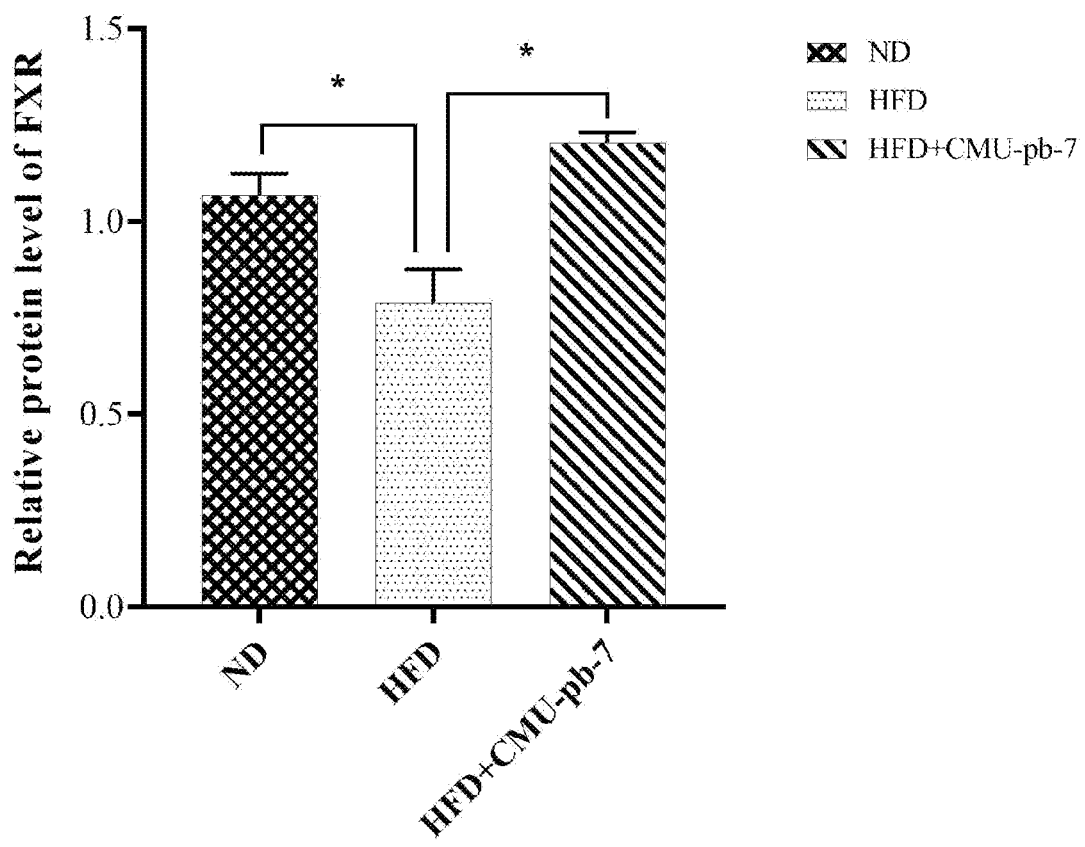
FIG. 24 shows liver FXR protein expression level detection results of a mouse with hyperlipidemia with a medical cell CMU-pb-7 of the present invention.
Figure 25:
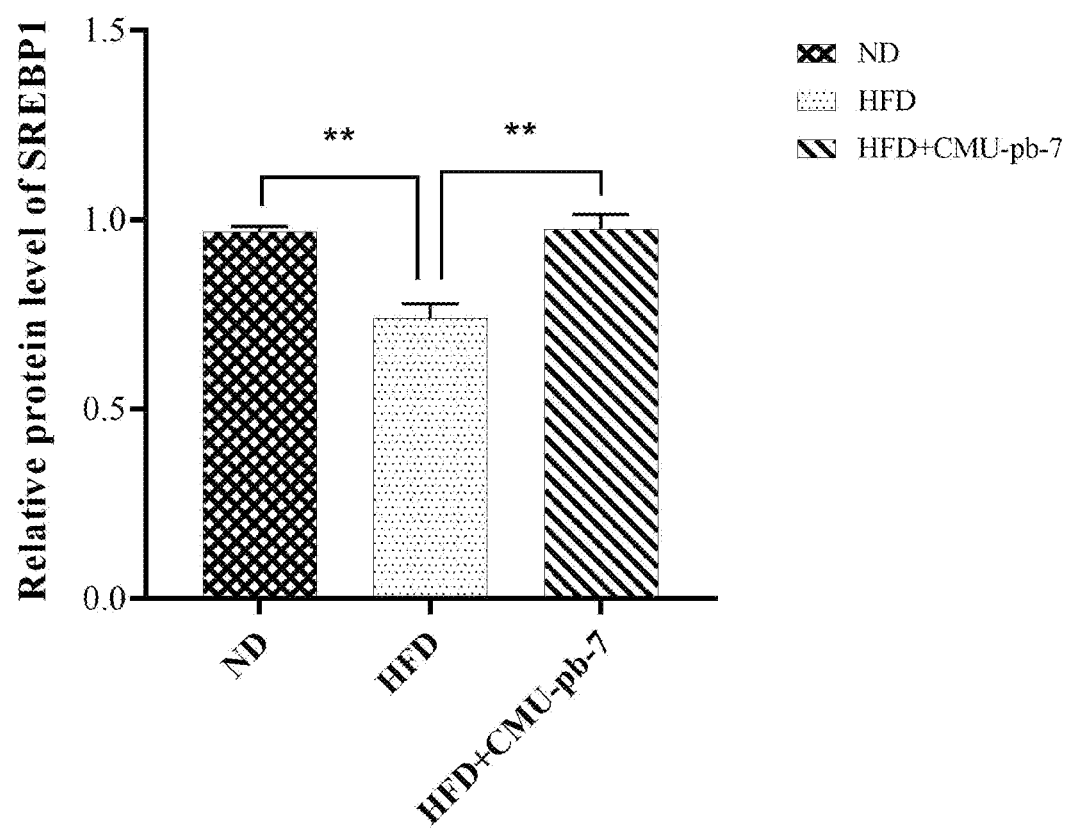
FIG. 25 shows liver SREBP1 protein expression level detection results of a mouse with hyperlipidemia with a medical cell CMU-pb-7 of the present invention.
Figure 26:
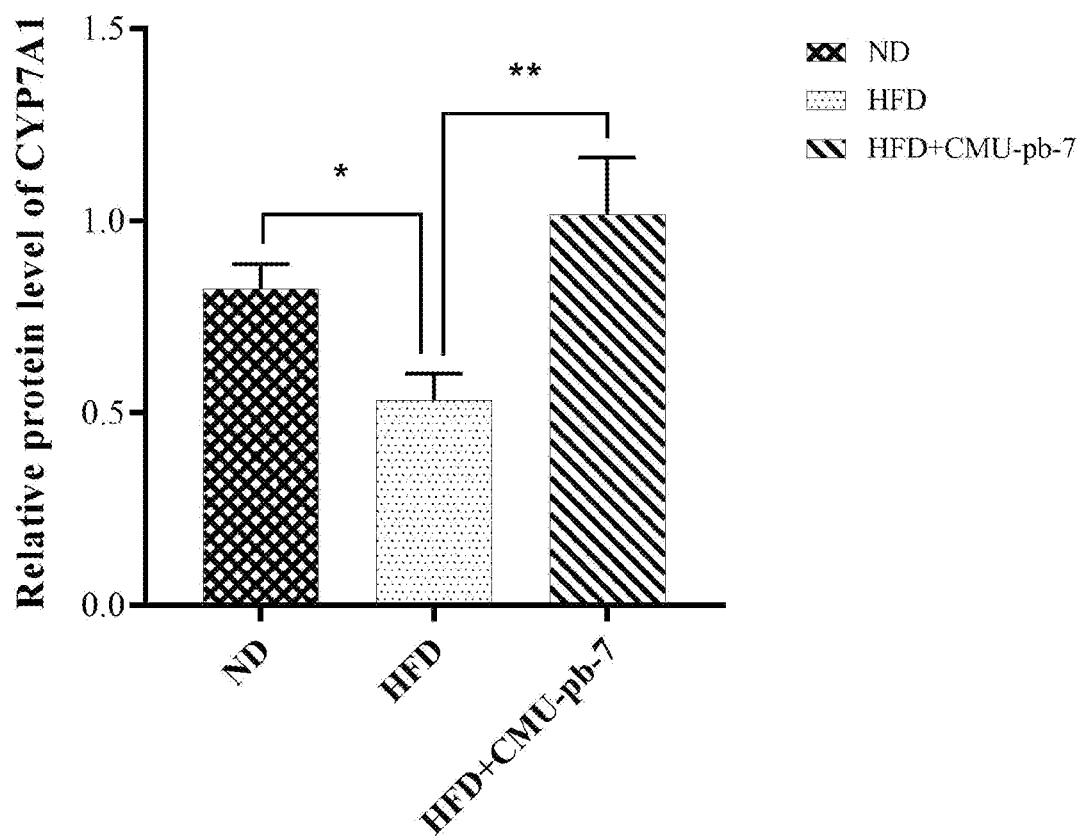
FIG. 26 shows liver CYP7A1 protein expression level detection results of a mouse with hyperlipidemia with a medical cell CMU-pb-7 of the present invention.

Ileum histological injury scores: 0, normal intestinal mucosa; 1, mild edema, telangiectasia and hyperemia under the epithelium at the top end of the intestinal mucosa; 2, the gap between the epithelial cells and the lamina propria of the intestinal mucosa is increased; 3, the top end of part of the lamina propria of the intestinal mucosa is exposed, and the epithelial cells are shed; 4, the lamina propria of the mucosa is exposed or the structure of glandular epithelium is absent, and telangiectasia and hyperemia occur, which may also be accompanied by inflammatory cell infiltration of the lamina propria; and 5, intestinal mucosa bleeding, ulcer and lamina propria disintegration. The assessment results are shown in FIG. 22, which show that: the ileum tissue injury scores of the mice in the HFD+CMU-pb-7 group are significantly lower than those in the HFD group, indicating that CMU-pb-7 can relieve the damage of the ileum tissue of mice with hyperlipidemia.

(11) Detection of Protein Expression Related to Lipid Metabolism in Mice with Hyperlipidemia 0.1 g of mouse liver tissue is added into lysate and homogenized, the total liver protein is extracted, and the concentration of the total protein is determined by the BCA method. 8% sodium dodecyl sulphate-polyacrylamide gel electrophoresis (SDS-PAGE) is prepared, 50 μg of protein is sampled, the electrophoretic voltage is set to 80 V, and the time is set to 90 min. The membrane transfer current is set to 300 mA, and the time is set to 90 min. After completion, the membrane is transferred to a PVDF membrane which is sealed with 2% BSA for 1 h, the sealing liquid is discarded, the membrane is washed for 3 times, primary antibodies of HMGCR (1:1000), FXR (1:1000), SREPB1 (1:1000), CYP7A1 (1:1000) and GAPDH (1:1000) are incubated and placed in a 4° C. refrigerator overnight, the membrane is washed with TBST for 3 times, and horseradish peroxidase is added to mark secondary antibodies (1:2000) for incubation at room temperature for 1 h. With GAPDH (1:1000) as an internal reference control, the imprinted bands of proteins are detected by ECL chemiluminescence, and the protein expression levels are analyzed according to the protein gray value. The experiment is repeated three times, and the average value is taken. The assessment results are shown in FIG. 23 to FIG. 26, which show that: compared with the HFD group, the HMGCR protein expression level of the mice in the HFD+CMU-pb-7 group is decreased, and the FXR, SREBP1 and CYP7A1 protein expression levels are increased, indicating that CMU-pb-7 can relieve the fatty change of liver by regulating the expression of key proteins of liver lipid metabolism.

The above description of the disclosed embodiments enables those skilled in the art to realize or use the present invention. Many modifications to these embodiments will be apparent to those skilled in the art. The general principle defined herein can be realized in other embodiments without departing from the spirit or scope of the present invention. Therefore, the present invention will not be limited to these embodiments shown herein, but will conform to the widest scope consistent with the principle and novel features disclosed herein.

What is claimed is:

1. A method of preparing a blood lipid-lowering drug, comprising:
providing a medical cell *Lactobacillus rhamnosus* CMU-pb-7, the medical cell *Lactobacillus rhamnosus* CMU-pb-7 being deposited at the China Center for Type Culture Collection (CCTCC) under accession number M 2022220,
wherein providing the medical cell *Lactobacillus rhamnosus* CMU-pb-7 comprises:
(1) collecting fresh feces of healthy people in a morning of a day through sampling, and separating fecal bacteria immediately;
(2) adding an MRS broth medium containing glycerol as a cryoprotectant to the separated fecal bacteria to obtain a crude fecal bacteria solution;
(3) adding the crude fecal bacteria solution into normal saline, and mixing thoroughly to a concentration of $10^{-3}$ to $10^{-7}$;
(4) applying the crude fecal bacterial solution to an MRS agar medium, a TPY agar medium and an M17 agar medium, and culturing at 37° C. under anaerobic conditions for 48 to 72 hours;

(5) selecting pure cultures of single colonies on corresponding agar media to obtain the medical cell *Lactobacillus rhamnosus* CMU-pb-7.

\* \* \* \* \*